(12) United States Patent
Strauss et al.

(10) Patent No.: US 9,750,668 B2
(45) Date of Patent: Sep. 5, 2017

(54) EMULSION CONCENTRATE

(75) Inventors: Gabriele Strauss, Düsseldorf (DE); Rolf Kawa, Monheim (DE); Petra Schulte, Köln (DE); Anja Stork, Köln (DE)

(73) Assignee: Cognis IP Management GmbH, Düsseldorf (DE)

( * ) Notice: Subject to any disclaimer, the term of this patent is extended or adjusted under 35 U.S.C. 154(b) by 1514 days.

(21) Appl. No.: 12/377,553

(22) PCT Filed: Aug. 6, 2007

(86) PCT No.: PCT/EP2007/006918
§ 371 (c)(1),
(2), (4) Date: Feb. 13, 2009

(87) PCT Pub. No.: WO2008/019773
PCT Pub. Date: Feb. 21, 2008

(65) Prior Publication Data
US 2011/0287073 A1    Nov. 24, 2011

(30) Foreign Application Priority Data

Aug. 14, 2006 (EP) ..................................... 06016953

(51) Int. Cl.
| A61K 8/86 | (2006.01) |
| A61K 8/02 | (2006.01) |
| A61K 8/06 | (2006.01) |
| A61K 8/31 | (2006.01) |
| A61K 8/37 | (2006.01) |
| A61Q 19/00 | (2006.01) |
| A61K 8/34 | (2006.01) |
| A61K 9/107 | (2006.01) |
| A61K 47/00 | (2006.01) |
| A61K 47/14 | (2017.01) |
| A61K 47/26 | (2006.01) |
| A61K 9/12 | (2006.01) |
| A61K 8/73 | (2006.01) |
| A61Q 19/10 | (2006.01) |

(52) U.S. Cl.
CPC .............. *A61K 8/06* (2013.01); *A61K 8/0208* (2013.01); *A61K 8/31* (2013.01); *A61K 8/342* (2013.01); *A61K 8/345* (2013.01); *A61K 8/37* (2013.01); *A61K 8/86* (2013.01); *A61Q 19/00* (2013.01); *A61Q 19/10* (2013.01)

(58) Field of Classification Search
CPC .......... A61K 8/31; A61K 8/06; A61K 8/0208; A61K 8/345; A61K 8/86; A61K 8/342; A61K 8/37; A61Q 19/00
See application file for complete search history.

(56) References Cited

U.S. PATENT DOCUMENTS

| 4,148,743 A | * | 4/1979 | Schubert | .................. C11D 9/40 510/152 |
| 5,494,938 A | * | 2/1996 | Kawa et al. | .................. 514/786 |
| 6,333,040 B1 | * | 12/2001 | Boyxen et al. | ............... 424/401 |
| 6,805,871 B1 | | 10/2004 | Benner et al. | ................. 424/401 |
| 2002/0010114 A1 | * | 1/2002 | Dufay et al. | .................. 510/130 |
| 2004/0258627 A1 | * | 12/2004 | Riedel et al. | ................... 424/47 |
| 2004/0258654 A1 | * | 12/2004 | Nielsen et al. | ............ 424/70.31 |
| 2006/0013783 A1 | | 1/2006 | Sebillotte-Arnaud et al. | ............................ 424/70.1 |
| 2006/0057168 A1 | * | 3/2006 | Larm et al. | .................... 424/400 |
| 2009/0082284 A1 | * | 3/2009 | Sorns et al. | .................... 514/23 |

FOREIGN PATENT DOCUMENTS

| DE | 19712033 | | 9/1998 |
| EP | 0693471 | | 1/1996 |
| EP | 0694521 | | 1/1996 |
| EP | 0723432 | | 7/1996 |
| EP | 0818450 | | 1/1998 |
| EP | 1106170 | | 6/2001 |
| EP | 1380279 | | 1/2004 |
| GB | 001043453 A | * | 9/1966 |
| WO | 92/07543 | | 5/1992 |
| WO | WO-95/10259 | | 4/1995 |

OTHER PUBLICATIONS

Allen et al., Journal of the American Oil Chemists Society, 76: 317-323 (1999).*
Volpo Fatty Acid Ethoxylates, Personal Care Brochure. Croda, Inc., (2001).*
Parkinson and Sherman, (Abstract) Journal of Colloid and Interface Science, 41: 328-330 (1972).*
"Humectants/Hydrotropes", BASF, downloaded from http://www.personal-care.basf.com/europe/by-product-group/humectants-hydrotropes, Feb. 8, 2016.*
"Isopropyl myristate", SC Johnson, downloaded from http://www.whatsinsidescjohnson.com/us/en/ingredients/isopropyl_myristate, Feb. 9, 2016.*

(Continued)

Primary Examiner — Kortney L Klinkel
Assistant Examiner — Lisbeth C Robinson
(74) Attorney, Agent, or Firm — Marshall, Gerstein & Borun LLP

(57) ABSTRACT

The present invention relates to an emulsion concentrate containing water-insoluble oil components (A), hydrophilic non-ionic emulsifiers (B), lipophilic co-emulsifiers (C), polyols (D) and water; which comprises less than 50% by weight of water-insoluble oil component (A), based on the total weight of the concentrate, and comprises components (A), (B) and (C) and (D) in a ratio by weight A:B:C:D=1:(0.25-0.6):(0.25-0.6):(0.45-0.65). The invention further relates to the use of these emulsion concentrates, and also to preparations and paper products, non-woven products or textile products for body care and personal cleansing, which comprise water-insoluble oil components (A), hydrophilic non-ionic emulsifiers (B), lipophilic co-emulsifiers (C), and polyols (D) in a ratio by weight A:B:C:D=1:(0.25-0.6):(0.25-0.6):(0.45-0.65).

16 Claims, No Drawings

(56) References Cited

OTHER PUBLICATIONS

Twenty Fourth Commision Directive 2000/6/EC of Feb. 29, 2000 adapting to technical progress Annexes II, III, IV, and VII to council Directive 78/768/EEC on the approximation of the laws of the member states relating to cosmetic products [on line], [retrieved on May 18, 2007]. Retrieved from the Internet, URL:https://webinsight.arielsearch.com/arielft/eudoc/reg/t04836.htm.

Finkel, P. Formulienrung Kosmetischer Sonnenschutzmittel. In: Parfumerie and kosmetik, 80. Jahrgang, Nr.3/99. p. 10-16.

Finkel, P. Formulienrung Kosmetischer Sonnenschutzmittel. In:SOFW-Journal, 122 Jahrgang 8/96 p. 543-548.

* cited by examiner

EMULSION CONCENTRATE

CROSS REFERENCE TO RELATED APPLICATIONS

This application is the National Phase entry of PCT/EP2007/006918, filed Aug. 6, 2007, which claims priority to EPO patent application number EP 06016953, filed Aug. 14, 2006, both of which are incorporated herein by reference in their entireties.

FIELD OF THE INVENTION

The invention relates to an emulsion concentrate which is flowable and pumpable at standard temperature, and to its use for producing cosmetic and pharmaceutical preparations.

BACKGROUND OF THE INVENTION

The production of emulsion-like preparations normally requires a considerable expenditure in terms of apparatus since the disperse phase has to be liquefied by heating and be dispersed in the continuous phase with the application of shear energy. There have already been various attempts to produce emulsion concentrates which can be diluted with the continuous phase without the introduction of heat and without shear work.

Thus, for example, EP 0 723 432 B1 discloses flowable emulsion concentrates which are flowable and pumpable at standard temperature and can be further processed with water and oil components and optionally further additives to give emulsion-like preparations without the introduction of heat and with the application of only a low stirring energy.

WO 92/07543 describes O/W emulsions which comprise alkyl polyglucosides and partial glycerides. A disadvantage of these emulsions is the low stability of these emulsions, especially at elevated temperatures. Furthermore, on account of their high viscosity, these emulsions are not pumpable or are pumpable only with difficulty.

US 2006/0013783 A1 describes finely divided cosmetic or dermatological O/W emulsions.

A disadvantage of the emulsion concentrates described in EP 0 723 432 B1 is their low storage stability at elevated temperatures, especially at temperatures above 40° C., and upon prolonged storage times. These conditions result in separation of the phases. Furthermore, there is a need for emulsion concentrates which comprise the lowest possible aqueous fraction since transportation and storage costs can thereby be reduced.

Surprisingly, it has been found that the emulsion concentrates of the present invention achieve these objects.

DETAILED DESCRIPTION OF PREFERRED EMBODIMENTS

The invention therefore provides an emulsion concentrate with a content of water-insoluble oil components (A), hydrophilic nonionic emulsifiers (B), lipophilic coemulsifiers (C), polyols (D) and water, which
    a. comprises less than 50% by weight of water-insoluble oil component (A)
       —based on the total weight of the concentrate—
    b. comprises the components (A), (B), (C) and (D) in the weight ratio A:B:C:D=1:(0.25-0.6):(0.25-0.6):(0.45-0.65).

The emulsion concentrate according to the invention is preferably flowable and pumpable at 20° C.

In this connection, flowable or pumpable is used to refer to those emulsion concentrates whose viscosity at 20° C. is below 20 Pa·s, measured using a Brookfield rotary viscometer (model RVF, spindle 4, 10 rpm).

Water-Insoluble Oil Component (A)

Suitable water-insoluble oil components (A) are all fatty substances or fatty substance mixtures which are liquid at 30° C., i.e. also mixtures of liquid and, dissolved therein, solid fatty substances or paraffins provided these mixtures are liquid at 30° C. or their viscosity (20° C.) is below 20 Pa·s (measured using a Brookfield rotary viscometer model RVF, spindle 4, 10 rpm).

Preferably suitable oil components (A) are the hydrocarbons which are liquid at 30° C., dialkyl ethers, fatty acid esters having 12-44 carbon atoms, dialkyl carbonates, Guerbet alcohols and silicone oils or mixtures thereof.

In one preferred embodiment of the invention, at least 60% by weight of the water-insoluble oil component (A) have an average polarity of greater than or equal to 20 mN/m and less than or equal to 30 mN/m. Particularly preferably, at least 70% by weight, in particular at least 80% by weight, of the water-insoluble oil component (A) have an average polarity of greater than or equal to 20 mN/m and less than or equal to 30 mN/m. The % by weight are based on the total amount of water-insoluble oil component (A).

The polarity of the water-insoluble oil component (A) is expressed via the interfacial tension. The interfacial tension is the force which acts on an imaginary line one meter in length in the interface between two phases. The physical unit for the interfacial tension is conventionally calculated from the force/length relationship and is usually expressed in mN/m (millinewtons divided by meters). It has a positive sign if it endeavors to reduce the interface; in the converse case, it has a negative sign. The interfacial tension can be determined, for example, in accordance with the ASTM method D971-99a (reapproved 2004).

As a result of the high fraction of water-insoluble oil component (A) of this polarity, especially stable emulsion concentrates are obtained.

The water-insoluble oil components (A) can comprise oils, fats, waxes and any desired mixtures thereof.

In one embodiment of the invention, the water-insoluble components (A) comprises at least one oil.

The term "oils" (used synonymously: oil component) is used to refer to water-insoluble organic compounds which are liquid at 30° C. and have a relatively low vapor pressure. The common feature of the oils is not their corresponding chemical constitution, but their similar physical consistency.

Suitable oil components are, for example, the classes of compound specified below provided these are liquid at 30° C. Thus, for example, Guerbet alcohols based on fatty alcohols having 6 to 18, preferably 8 to 10, carbon atoms (e.g. Eutanol® G), esters of linear $C_6$-$C_{22}$-fatty acids with linear or branched $C_6$-$C_{22}$-fatty alcohols or esters of branched $C_6$-$C_{13}$-carboxylic acids with linear or branched $C_6$-$C_{22}$-fatty alcohols, such as, for example, myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate, erucyl erucate and hexyldecyl stearate (Eutanol® G 16 S). Also suitable are esters of linear $C_6$-$C_{22}$-fatty acids with branched alcohols, in particular 2-ethylhexanol, esters of $C_3$-$C_{38}$-alkylhydroxycarboxylic acids with linear or branched $C_6$-$C_{22}$-fatty alcohols—in particular dioctyl malate—, esters of linear and/or branched fatty acids with polyhydric alcohols (such as, for example, propylene glycol, dimerdiol or trimertriol) and/or Guerbet alcohols, triglycerides based on $C_6$-$C_{10}$-fatty acids, liquid mono-/di-/triglyceride mixtures based on $C_6$-$C_{18}$-fatty acids, esters of $C_6$-$C_{22}$-fatty alcohols and/or Guerbet alcohols with aromatic carboxylic acids, in particular benzoic acid, esters of $C_2$-$C_{12}$-dicarboxylic acids with linear or branched alcohols having 1 to 22 carbon atoms or polyols having 2 to 10 carbon atoms and 2 to 6 hydroxyl groups, vegetable oils, branched primary alcohols, substituted cyclohexanes, such as, for example, 1,3-dialkylcyclohexanes, linear and branched $C_6$-$C_{22}$-fatty alcohol carbonates, such as, for example, Dicaprylyl Carbonate (Cetiol® CC), Guerbet carbonates based on fatty alcohols having 6 to 18, preferably 8 to 10, carbon atoms, esters of benzoic acid with linear and/or branched $C_6$-$C_{22}$-alcohols (e.g. Finsolv® TN), linear or branched, symmetrical or asymmetrical dialkyl ethers having 6 to 22 carbon atoms per alkyl group, such as, for example, dicaprylyl ether (Cetiol® OE), ring-opening products of epoxidized fatty acid esters with polyols (Hydagen® HSP, Sovermol® 750, Sovermol® 1102), silicone oils (cyclomethicones, silicon methicone types etc. and/or aliphatic or naphthenic hydrocarbons, such as, for example, like mineral oil, Vaseline, petrolatum, squalane, squalene or dialkylcyclohexanes.

Suitable silicone oils are, besides dimethylpolysiloxanes, methylphenylpolysiloxanes and cyclic silicones, also amino-, fatty-acid-, alcohol-, polyether-, epoxy-, fluorine-, glycoside- and/or alkyl-modified silicone compounds which, at room temperature, may be present either as liquid or else in resin form. Also suitable are simethicones, which are mixtures of dimethicones having an average chain length of from 200 to 300 dimethylsiloxane units and silicon dioxide or hydrogenated silicates.

Suitable oil components are also polycarbonates, as described, for example, in WO 03/041676, which is incorporated herein by reference.

A particularly suitable polycarbonate is that under the INCI name Hydrogenated Dimer Dilinoleyl/Dimethyl-carbonate Copolymer, which is available as the commercial product Cosmedia® DC from Cognis Deutschland GmbH & Co. KG.

Dialkyl ethers, dialkyl carbonates, triglyceride mixtures and esters of C6-C22-fatty acids and C6-C22-fatty alcohols, polycarbonates or a mixture of these substances are particularly well suited according to the invention as oil components. The dialkyl carbonates and dialkyl ethers may be symmetrical or asymmetrical, branched or unbranched, saturated or unsaturated and can be prepared by reactions which are sufficiently known from the prior art.

According to the invention, it is also possible to use, inter alia, hydrocarbons, preferably having a chain length of 8 to 40 carbon atoms. They may be branched or unbranched, saturated or unsaturated. Among these, branched, saturated C8-C40-alkanes are preferred. It is possible to use either pure substances or substance mixtures. They are usually substance mixtures of different isomeric compounds. Compositions which have alkanes with 10 to 30, preferably 12 to 20, and particularly preferably 16 to 20, carbon atoms are particularly suitable, and among these a mixture of alkanes which comprises at least 10% by weight of branched alkanes, based on the total amount of the alkanes. These are preferably branched, saturated alkanes. Mixtures of alkanes which comprise more than 1% by weight of 5,8-diethyldodecane and/or more than 1% by weight of didecene are particularly highly suitable.

In one embodiment of the invention, the water-insoluble oil component (A) comprises at least one wax.

The term wax (used synonymously: wax component) is usually understood as meaning all natural or synthetically obtained substances and substance mixtures with the following properties: they are of solid to brittle hard consistency, coarse to finely divided, transparent to opaque and melt above 30° C. without decomposition. Even a little above the melting point, they are of low viscosity and not thread-drawing and exhibit a strongly temperature-dependent consistency and solubility. According to the invention, it is possible to use a wax component or a mixture of wax components which melt at 30° C. or above.

According to the invention, waxes which can be used are also fats and fat-like substances with wax-type consistency provided they have the required melting point. These include, inter alia, fats (triglycerides), and natural and synthetic waxes or any desired mixtures of these substances.

Fats are understood as meaning triacylglycerols, i.e. the triple esters of fatty acids with glycerol. Preferably, they contain saturated, unbranched and unsubstituted fatty acid radicals. These may also be mixed esters, i.e. triple esters of glycerol with various fatty acids.

So-called hydrogenated fats and oils, which are obtained by partial hydrogenation, can be used according to the invention. Vegetable hydrogenated fats and oils are preferred, e.g. hydrogenated castor oil, peanut oil, soybean oil, colza oil, rapeseed oil, cottonseed oil, soybean oil, sunflower oil, palm oil, palm kernel oil, linseed oil, almond oil, corn oil, olive oil, sesame oil, cocobutter and coconut fat.

The triple esters of glycerol with $C_{12}$-$C_{60}$-fatty acids and in particular $C_{12}$-$C_{36}$-fatty acids are inter alia suitable. These include hydrogenated castor oil, a triple ester of glycerol and a hydroxystearic acid, which is commercially available, for example, under the name Cutina® HR. Likewise suitable are glycerol tristearate, glycerol tribehenate (e.g. Syncrowax® HRC), glycerol tripalmitate or the triglyceride mixtures known under the name Syncrowax® HGLC, with the proviso that the melting point of the wax component or of the mixture is 30° C. or above.

According to the invention, it is possible to use, for example, natural vegetable waxes, such as candelilla wax, carnauba wax, Japan wax, esparto grass wax, cork wax, guaruma wax, rice germ oil wax, sugarcane wax, ouricury wax, montan wax, sunflower wax, fruit waxes such as orange waxes, lemon waxes, grapefruit wax, bayberry wax, and animal waxes, such as, for example, beeswax, shellac wax, spermaceti, wool wax and uropygial fat. Within the context of the invention, it may be advantageous to use hydrogenated or hardened waxes. The natural waxes which can be used according to the invention also include the mineral waxes, such as, for example, ceresine and ozokerite, or the petrochemical waxes, such as, for example, petrolatum, paraffin waxes and microwaxes. As wax component, it is also possible to use chemically modified waxes, in particular the hard waxes, such as, for example montan ester waxes, sasol waxes and hydrogenated jojoba waxes. The synthetic waxes which can be used according to the invention include, for example, wax-like polyalkylene waxes and polyethylene glycol waxes. Vegetable waxes are preferred according to the invention.

The wax component can likewise be selected from the group of wax esters provided they do not have a free OH group, of saturated and/or unsaturated, branched and/or unbranched alkanecarboxylic acids and saturated and/or unsaturated, branched and/or unbranched alcohols, from the group of esters of aromatic carboxylic acids, dicarboxylic acids, tricarboxylic acids and hydroxycarboxylic acids (e.g. 12-hydroxystearic acid) and saturated and/or unsaturated, branched and/or unbranched alcohols, and also from the group of lactides of long-chain hydroxycarboxylic acids. Examples of such esters are the $C_{16}$-$C_{40}$-alkyl stearates, $C_{20}$-$C_{40}$-alkyl stearates (e.g. Kesterwachs® K82H), $C_{20}$-$C_{40}$-dialkyl esters of dimer acids, $C_{18}$-$C_{38}$-alkylhydroxystearoyl stearates or $C_{20}$-$C_{40}$-alkyl erucates. It is also possible to use $C_{30}$-$C_{50}$-alkyl beeswax, tristearyl citrate, triisostearyl citrate, stearyl heptanoate, stearyl octanoate, trilauryl citrate, ethylene glycol dipalmitate, ethylene glycol distearate, ethylene glycol di(12-hydroxystearate), stearyl stearate, palmityl stearate, stearyl behenate, cetearyl behenate and behenyl behenate.

In one preferred embodiment of the invention, the water-insoluble oil component (A) comprises at least one oil component selected from the group consisting of hydrocarbons, dialkyl ethers, dialkyl carbonates, triglyceride mixtures, esters of C6-C22-fatty acids and C6-C22-fatty alcohols, polycarbonates or a mixture of these substances, silicone oils and mixtures thereof.

The amount of water-insoluble oil component (A) is less than 50% by weight, preferably less than 45% by weight, in particular less than 40% by weight, based on the total weight of the emulsion concentrate.

When calculating the amount of component (A), the hydrophilic nonionic emulsifiers (B) and the coemulsifiers (C) are not taken into consideration.

Hydrophilic Nonionic Emulsifiers (B)

Suitable hydrophilic nonionic emulsifiers (B) are preferably addition products of ethylene oxide onto linear fatty alcohols, fatty acids, fatty acid partial glycerides, sorbitan fatty acid esters or alkyl (oligo)glycosides, where these compounds have an HLB value of 11-20.

Particularly preferably suitable hydrophilic nonionic emulsifiers (B) are addition products of ethylene oxide onto linear fatty alcohols, fatty acids, fatty acid partial polyglycerides, or sorbitan fatty acid esters with an HLB value of 11-20.

Very particularly suitable hydrophilic nonionic emulsifiers (B) are addition products of ethylene oxide onto linear fatty alcohols with an HLB value of 11-20. Preferably suitable hydrophilic nonionic emulsifiers (B) are the addition products of 8-30 mol of ethylene oxide onto linear fatty alcohols having 12-22 carbon atoms.

Here, the HLB value should be understood as meaning the value according to formula I $$HLB = \frac{100 - L}{5} \qquad (I)$$

in which L is the fraction (in % by weight) of the lipophilic alkyl or acyl groups in the ethylene oxide addition products.

The emulsion concentrates can comprise the components (B) in amounts of from 1 to 25% by weight, preferably 5 to 20% by weight, in particular 8 to 12% by weight—based on the total weight of the concentrate.

Lipophilic Coemulsifiers (C)

The lipophilic coemulsifiers (C) are nonionic, polar lipid substances with one or more hydroxyl groups which are insoluble or only dispersible in water and which, on account of their low hydrophilicity, are on their own not suitable for the preparation of oil-in-water emulsions.

Lipophilic coemulsifiers preferably have an HLB value of <10.

The $C_{12}$-$C_{50}$-fatty alcohols can be used as lipophilic coemulsifier (C). Of suitability in particular are $C_{12}$-$C_{24}$-fatty alcohols, which can also be used in combination with the C12-C24 partial esters of polyhydric alcohols. The fatty alcohols can be obtained from natural fats, oils and waxes, such as, for example, myristyl alcohol, 1-pentadecanol, cetyl alcohol, 1-heptadecanol, stearyl alcohol, 1-nonadecanol, arachidyl alcohol, 1-heneicosanol, behenyl alcohol, brassidyl alcohol, lignoceryl alcohol, ceryl alcohol or myricyl alcohol. According to the invention, preference is given to saturated unbranched fatty alcohols. However, also unsaturated, branched or unbranched fatty alcohols can be used according to the invention as wax component provided they have the required melting point. According to the invention, it is also possible to use fatty alcohol cuts, as are produced during the reduction of naturally occurring fats and oils, such as, for example, bovine tallow, peanut oil, colza oil, cottonseed oil, soybean oil, sunflower oil, palm kernel oil, linseed oil, castor oil, corn oil, rapeseed oil, sesame oil, cocoa butter and coconut fat. However, it is also possible to use synthetic alcohols, e.g. the linear, even-numbered fatty alcohols of the Ziegler synthesis) (Alfols®) or the partially branched alcohols from the oxo synthesis) (Dobanols®). Of particularly preferred suitability according to the invention are $C_{14}$-$C_{22}$-fatty alcohols, which are marketed, for example, by Cognis Deutschland GmbH under the name Lanette® 16 ($C_{16}$-alcohol), Lanette® 14 ($C_{14}$-alcohol), Lanette® O ($C_{16}$/$C_{18}$-alcohol) and Lanette® 22 ($C_{18}$/$C_{22}$-alcohol). Fatty alcohols give the compositions a drier skin feel than triglycerides and are therefore preferred over the latter.

According to the invention, suitable coemulsifiers (C) are in particular those of the type of saturated fatty alcohols having 16-22 carbon atoms, e.g. cetyl alcohol, stearyl alcohol, arachidyl alcohol or behenyl alcohol or mixtures of these alcohols, as are obtained during the industrial hydrogenation of vegetable and animal fatty acids having 16-22 carbon atoms or of the corresponding fatty acid methyl esters.

$C_{14}$-$C_{40}$-Fatty acids or mixtures thereof can also be used as lipophilic coemulsifier (C). These include, for example, myristic acid, pentadecanoic acid, palmitic acid, margaric acid, stearic acid, nonadecanoic acid, arachic acid, behenic acid, lignoceric acid, cerotic acid, melissic acid, erucic acid and elaeostearic acid, and also substituted fatty acids, such as, for example, 12-hydroxystearic acid, and the amides or monoethanolamides of fatty acids, this list being exemplary and nonlimiting in character.

Furthermore, suitable coemulsifiers (C) are partial esters of polyhydric alcohols, in particular of a polyol having 3-6 carbon atoms and saturated fatty acids having 12-24 carbon atoms, preferably having 14 to 22 carbon atoms. Such partial esters are, for example, the monoglycerides of palmitic acid and/or stearic acid, the sorbitan mono- and/or diesters of myristic acid, palmitic acid, stearic acid or of mixtures of these fatty acids, the monoesters of trimethylolpropane, erythritol or pentaerythritol and saturated fatty acids having 12 to 22 carbon atoms, preferably having 14-22 carbon atoms. Monoesters are also understood as meaning the industrial monoesters which are obtained by esterifying 1 mol of polyol with 1 mol of fatty acid and which constitute a mixture of monoester, diester and unesterified polyol. Saturated fatty alcohols having 16-22 carbon atoms or partial esters of polyols having 3-6 carbon atoms and fatty acids having 14-22 carbon atoms are particularly highly suitable. Suitable partial esters are in particular partial esters of pentaerythritol with C16/C18 fatty alcohols, as are commercially available, for example, under the trade name Cutina® PES (Cognis Deutschland GmbH & Co. KG).

The lipophilic coemulsifier (C) used may be, for example, partial esters of C12 to C24 fatty acids, preferably C12-C22 fatty acids with polyhydric alcohols, in particular with glycerol:

The polyhydric alcohols which are of suitability here preferably have 2 to 15 carbon atoms and at least two hydroxyl groups. The polyols can also contain further functional groups, in particular amino groups, and/or be modified with nitrogen. Typical examples are:

glycerol alkylene glycols, such as, for example, ethylene glycol, diethylene glycol, propylene glycol, butylene glycol, hexylene glycol, and polyethylene glycols with an average molecular weight of from 100 to 1000 daltons;

technical-grade oligoglycerol mixtures with a degree of self-condensation of from 1.5 to 10, such as, for example, technical-grade diglycerol mixtures with a diglycerol content of from 40 to 50% by weight;

methyol compounds, such as, in particular, trimethylolethane, trimethylolpropane, trimethylolbutane, pentaerythritol and dipentaerythritol;

short-chain alkyl glucosides, in particular those having 1 to 8 carbon atoms in the alkyl radical, such as, for example, methyl glucoside and butyl glucoside;

sugar alcohols having 5 to 12 carbon atoms, such as, for example, sorbitol or mannitol, sugars having 5 to 12 carbon atoms, such as, for example, glucose or sucrose;

amino sugars, such as, for example, glucamine;

dialcohol amines, such as diethanolamine or 2-amino-1,3-propanediol.

Typical examples of suitable partial glycerides are mono- and/or diglycerides of C12 to C22 fatty acids with glycerol, and technical-grade mixtures thereof. For example, mention may be made of long-chain hydroxy fatty acid monoglycerides, long-chain hydroxy fatty acid diglycerides, isostearic acid monoglyceride, isostearic acid diglyceride, oleic acid monoglyceride, oleic acid diglyceride, ricinoleic acid moglyceride, ricinoleic acid diglyceride, linoleic acid monoglyceride, linoleic acid diglyceride, linolenic acid monoglyceride, linolenic acid diglyceride, erucic acid monoglyceride, erucic acid diglyceride.

Typical examples of suitable partial glycerides are mono- and/or diglycerides of dicarboxylic acids having 4 to 8 carbon atoms with glycerol, and technical-grade mixtures thereof. Those partial glycerides which have a melting point of >30° C. are particularly suitable. For example, mention may be made of tartaric acid monoglyceride, tartaric acid diglyceride, citric acid monoglyceride, citric acid diglyceride, malic acid monoglyceride, malic acid diglyceride, and technical-grade mixtures thereof which can also comprise small amounts of triglyceride to a secondary degree from the production process.

According to the invention, lipophilic coemulsifiers (C) which can be used are in particular mono- and diglycerides and mixtures of these partial glycerides. The glyceride mixtures which can be used according to the invention include the products Novata® AB and Novata® B (mixture of $C_{12}$-$C_{18}$-mono-, di- and triglycerides) and also Cutina® MD or Cutina® GMS (glyceryl stearate) marketed by Cognis Deutschland GmbH & Co. KG.

Addition products of from 1 to 30 mol, preferably 5 to 10 mol, of ethylene oxide onto the specified partial glycerides are likewise suitable.

Lipophilic coemulsifiers (C) which can be used are partial esters of glycerol and/or sorbitan with unsaturated, linear or saturated, branched fatty acids having 12 to 22 carbon atoms and/or hydroxycarboxylic acids having 3 to 18 carbon atoms, provided they have a melting point of >30° C.

Sorbitan Esters

Sorbitan esters which can be used are, for example, the following compounds. Sorbitan esters which have a melting point of >30° C. are particularly suitable.

Sorbitan esters are sorbitan monoisostearate, sorbitan sesquiisostearate, sorbitan diisostearate, sorbitan triisostearate, sorbitan monooleate, sorbitan sesquioleate, sorbitan dioleate, sorbitan trioleate, sorbitan monoerucate, sorbitan sesquierucate, sorbitan dierucate, sorbitan trierucate, sorbitan monoricinoleate, sorbitan sesquiricinoleate, sorbitan diricinoleate, sorbitan triricinoleate, sorbitan monohydroxystearate, sorbitan sesquihydroxystearate, sorbitan dihydroxystearate, sorbitan trihydroxystearate, sorbitan monotartrate, sorbitan sesquitartrate, sorbitan ditartrate, sorbitan tritartrate, sorbitan monocitrate, sorbitan sesquicitrate, sorbitan dicitrate, sorbitan tricitrate, sorbitan monomaleate, sorbitan sesquimaleate, sorbitan dimaleate, sorbitan trimaleate, and technical-grade mixtures thereof. Addition products of from 1 to 30 mol, preferably 5 to 10 mol, of ethylene oxide onto the specified sorbitan esters are likewise suitable.

Polyglycerol Esters

Polyglycerol esters which can be used are, for example, the following compounds. Polyglycerol esters which have a melting point of >30° C. are particularly suitable.

Typical examples of suitable polyglycerol esters are polyglyceryl-4 diisostearate/polyhydroxystearate/sebacate (Isolan GPS), polyglyceryl-2 dipolyhydroxystearate (Dehymuls PGPH), polycerol-3 diisostearate (Lameform TGI), polyglyceryl-4 isostearate (Isolan GI 34), polyglyceryl-3 oleate, diisostearoyl polyglyceryl-3 diisostearate (Isolan PDI), polyglyceryl-3 methylglucose distearate (Tego Care 450), polyglyceryl-3 beeswax (Cera Bellina), polyglyceryl-4 caprate (Polyglycerol Caprate T2010/90), polyglyceryl-3 cetyl ether (Chimexane NL), polyglyceryl-3 distearate (Cremophor GS 32) and polyglyceryl polyricinoleate (Admul WOL 1403), polyglyceryl dimerate isostearate, and mixtures thereof. Examples of further suitable polyesters are the mono-, di- and triesters of trimethylolpropane or pentaerythritol with lauric acid, coconut fatty acid, tallow fatty acid, palmitic acid, stearic acid, oleic acid, behenic acid and the like optionally reacted with 1 to 30 mol of ethylene oxide.

The emulsion concentrates can comprise the components (C) in the amount from amounts of from 1 to 25% by weight, preferably 5 to 20% by weight, in particular 8 to 15% by weight—based on the total weight of the concentrate.

Polyols (D)

Polyols is the term used to refer to polyhydric alcohols, i.e. organic compounds, which carry at least 2 alcoholic hydroxyl groups in the molecule. In one embodiment of the invention, the polyols contain 2 to 6 hydroxyl groups per molecule. In one embodiment of the invention, the polyols used are low molecular polyhydric alcohols, i.e. compounds which contain 2 to 18, in particular 2 to 10, preferably 2 to 6, carbon atoms.

In one preferred embodiment of the invention, the polyols (D) used are compounds which carry at least 2 hydroxyl groups per molecule and consist of 2 to 18, preferably 2 to 10, in particular of 2 to 6, carbon atoms.

In one preferred embodiment of the invention, the polyols (D) used are compounds which carry 2 to 6 hydroxyl groups per molecule.

Particular preference is given to polyols (D) which carry 2 to 6 hydroxyl groups per molecule and consist of 2 to 6 carbon atoms.

Polyols (D) which can be used are either individual polyols or else mixtures of any desired polyols. In one preferred embodiment, the polyols used are mixtures of at least 2, in particular at least 3, polyols.

The polyols (D) can also comprise further functional groups, in particular amino groups, and/or be modified with nitrogen. In one preferred embodiment, the polyols do not contain any further functional groups apart from the hydroxyl groups.

Typical examples of polyols to be used according to the invention are:

glycerol, diglycerol, triglycerol, tetraglycerol alkylene glycols, such as, for example, ethylene glycol, diethylene glycol, triethylene glycol, 1,2-propylene glycol, 1,3-propylene glycol, butylene glycol, hexylene glycol, and polyethylene glycols with an average molecular weight of from 100 to 1000 daltons;

technical-grade oligoglycerol mixtures with a degree of self-condensation of from 1.5 to 10, such as, for example, technical-grade diglycerol mixtures with a diglycerol content of from 40 to 50% by weight;

methyol compounds, such as, in particular, trimethylolethane, trimethylolpropane, trimethylolbutane, pentaerythritol and dipentaerythritol;

short-chain alkyl glucosides, in particular those with 1 to 8 carbon atoms in the alkyl radical, such as, for example, methyl glucoside and butyl glucoside;

sugar alcohols having 5 to 12 carbon atoms, such as, for example, erythritol, arabitol, adonitol (synonym ribitol), xylitol, sorbitol, mannitol and dulcitol (synonym galactitol).

sugars having 5 to 12 carbon atoms, such as, for example, glucose or sucrose;

amino sugars, such as, for example, glucamine;

dialcohol amines, such as diethanolamine or 2-amino-1,3-propanediol.

In one preferred embodiment of the invention, the polyol (D) used is at least one compound selected from the group consisting of glycerol, 1,2-propylene glycol, sorbitol, butylene glycol and hexylene glycol.

The emulsion concentrates can comprise the components (D) in amounts of from 1 to 25% by weight, preferably 5 to 20% by weight, in particular 8 to 15% by weight—based on the total weight of the concentrate.

Aqueous Fraction

In one preferred embodiment of the invention, the emulsion concentrates according to the invention comprise 35 to 55% by weight of aqueous fraction, based on the total weight of the emulsion concentrate.

Further Constituents

The emulsion concentrates according to the invention can comprise further constituents, such as, for example, preservatives, biogenic active ingredients, UV photoprotective filters, thickeners, superfatting agents, stabilizers, polymers, antioxidants, deodorants, film formers, swelling agents, insect repellents, hydrotropes, solubilizers, perfume oils, dyes etc. The amounts of the particular additives are dependent on the intended use.

If further constituents fall under the definition of the water-insoluble oil components (A), they are taken into consideration when calculating the ratios of (A):(B):(C):(D) by adding them to the components (A). This is true for all further constituents, but is especially relevant for lipophilic UV photoprotective filters and perfume oils.

The emulsion concentrates according to the invention usually comprise the further constituents in amounts of ≤25% by weight, in particular ≤20% by weight, based on the total amount of the concentrate.

Suitable preservatives are, for example, phenoxyethanol, formaldehyde solution, parabens, mixtures of phenoxyethanol and ethylhexylglycerol (as are available, for example, under the trade name Euxyl PE 9010) or sorbic acid, and the silver complexes known under the name Surfacine® and the further substance classes listed in Appendix 6, Part A and B of the Cosmetics Ordinance.

In one preferred embodiment of the invention, the preservative is selected from the group consisting of phenoxyethanol, formaldehyde solution, parabens, organic acids and mixtures thereof, optionally in combination with pentanediol and/or ethylhexylglycerol.

In one embodiment of the invention, the emulsion concentrates according to the invention comprise at least one UV photoprotective filter as further constituent.

According to the invention, suitable UV photoprotective factors are organic substances (photoprotective filters) which are crystalline or liquid at room temperature and which are able to absorb ultraviolet rays and release the absorbed energy again in the form of longer-wave radiation, e.g. heat. UV filters may be oil-soluble or water-soluble. Examples of typical oil-soluble UV-B filters and/or broad spectrum UV A/B filters are:

3-benzylidenecamphor or 3-benzylidenenorcamphor (Mexoryl SDS 20) and derivatives thereof, e.g. 3-(4-methylbenzylidene)camphor as described in EP 0693471 B1;

3-(4'-trimethylammonium)benzylidenebornan-2-one methyl sulfate (Mexoryl SO)

3,3'-(1,4-phenylenedimethine)bis(7,7-dimethyl-2-oxobicyclo[2.2.1]heptane-1-methanesulfonic acid) and salts (Mexoryl SX)

3-(4'-sulfo)benzylidenebornan-2-one and salts (Mexoryl SL)

polymer of N-{(2 and 4)-[2-oxoborn-3-ylidene)methyl]benzyl]acrylamide (Mexoryl SW)

2-(2H-benzotriazol-2-yl)-4-methyl-6-(2-methyl-3-(1,3,3,3-tetramethyl-1-(trimethylsilyloxy)-disiloxanyl)propyl)phenol (Mexoryl XL)

4-aminobenzoic acid derivatives, preferably 2-ethylhexyl 4-(dimethylamino)benzoate, 2-octyl 4-(dimethylamino)benzoate and amyl 4-(dimethylamino)-benzoate;

esters of cinnamic acid, preferably 2-ethylhexyl 4-methoxycinnamate, propyl 4-methoxycinnamate, isoamyl 4-methoxycinnamate, 2-ethylhexyl 2-cyano-3,3-phenylcinnamate (octocrylene);

esters of salicylic acid, preferably 2-ethylhexyl salicylate, 4-isopropylbenzyl salicylate, homomenthyl salicylate;

derivatives of benzophenone, preferably 2-hydroxy-4-methoxybenzophenone, 2-hydroxy-4-methoxy-4'-methyl-benzophenone, 2,2'-dihydroxy-4-methoxybenzophenone;

esters of benzalmalonic acid, preferably di-2-ethylhexyl 4-methoxybenzmalonate;

triazine derivatives, such as, for example, 2,4,6-trianilino (p-carbo-2'-ethyl-1'-hexyloxy)-1,3,5-triazine and 2,4,6-tris[p-(2-ethylhexyloxycarbonyl)-anilino]-1,3,5-triazine (Uvinul T 150), as described in EP 0818450 A1, or bis(2-ethylhexyl) 4,4'-[(6-[4-((1,1-dimethylethyl)aminocarbonyl)phenylamino]-1,3,5-triazine-2,4-diyl)diimino]bisbenzoate (Uvasorb® HEB);

2,2(-methylenebis(6-(2H-benzotriazol-2-yl)-4-(1,1,3,3-tetramethylbutyl)phenol (Tinosorb M);

2,4-bis[4-(2-ethylhexyloxy)-2-hydroxyphenyl]-6-(4-methoxyphenyl)-1,3,5-triazine (Tinosorb S);

propane-1,3-diones, such as, for example, 1-(4-tert-butylphenyl)-3-(4' methoxyphenyl)propane-1,3-dione;

ketotricyclo(5.2.1.0)decane derivatives, as described in EP 0694521 B1;

dimethicodiethyl benzalmalonates (Parsol SLX).

Suitable water-soluble UV filters are:

2-phenylbenzimidazole-5-sulfonic acid and alkali metal, alkaline earth metal, ammonium, alkylammonium, alkanolammonium and glucammonium salts thereof;

2,2(-(1,4-phenylene)bis(1H-benzimidazole-4,6-disulfonic acid, monosodium salt) (Neo Heliopan AP)

sulfonic acid derivatives of benzophenones, preferably 2-hydroxy-4-methoxybenzophenone-5-sulfonic acid and its salts;

sulfonic acid derivatives of 3-benzylidenecamphor, such as, for example, 4-(2-oxo-3-bornylidenemethyl)-benzenesulfonic acid and 2-methyl-5-(2-oxo-3-bornylidene)sulfonic acid and salts thereof.

Suitable typical UV-A filters are in particular derivatives of benzoylmethane, such as, for example, 1-(4'-tert-butylphenyl)-3-(4'-methoxyphenyl)propane-1,3-dione, 4-tert-butyl-4'-methoxydibenzoylmethane (Parsol® 1789), 1-phenyl-3-(4'-isopropylphenyl)propane-1,3-dione, and enamine compounds, as described in DE 19712833 A1 (BASF), and also benzoic acid, 2-[4-(diethylamino)-2-hydroxybenzoyl], hexyl ester (Uvinul® A plus).

The UV-A and UV-B filters can of course also be used in mixtures. Particularly favorable combinations consist of the derivatives of benzoylmethane, e.g. 4-tert-butyl-4'-methoxydibenzoylmethane (Parsol® 1789) and 2-ethylhexyl 2-cyano-3,3-phenylcinnamate (octocrylene) in combination with esters of cinnamic acid, preferably 2-ethylhexyl 4-methoxycinnamate and/or propyl 4-methoxycinnamate and/or isoamyl 4-methoxycinnamate. Such combinations are advantageously combined with water-soluble filters such as, for example, 2-phenylbenzimidazole-5-sulfonic acid and alkali metal, alkaline earth metal, ammonium, alkylammonium, alkanolammonium and glucammonium salts thereof.

According to the invention, preference is given to UV photoprotective filters selected from Appendix VII of the European Cosmetics Legislation ($24^{th}$ Adapting Commission Directive, Feb. 29, 2000).

Besides the specified soluble substances, insoluble photoprotective pigments, namely finely disperse metal oxides and/or salts are suitable for this purpose. Examples of suitable metal oxides are in particular zinc oxide and titanium dioxide and in addition oxides of iron, zirconium, silicon, manganese, aluminum and cerium, and mixtures thereof. Salts which can be used are silicates (talc), barium sulfate or zinc stearate. The oxides and salts are used in the form of the pigments for skincare and skin-protecting emulsions and also for decorative cosmetics. The particles should have an average diameter of less than 100 nm, preferably between 5 and 50 nm and in particular between 15 and 30 nm. They can have a spherical shape, although it is also possible to use those particles which have an ellipsoidal shape or a shape which deviates in some other way from the spherical configuration. The pigments can also be present in surface-treated, i.e. hydrophilicized or hydrophobicized, form. Typical examples are coated titanium dioxides, such as, for example, titanium dioxide T 805 (Degussa) or Eusolex® T, Eusolex® T-2000, Eusolex® T-Aqua, Eusolex® AVO, Eusolex® T-ECO, Eusolex® T-OLEO and Eusolex® T-S (Merck). Suitable hydrophobic coating compositions here are primarily silicones and, of these, specifically trialkoxyoctylsilanes or simethicones. In sunscreen compositions, preference is given to using so-called micropigments or nanopigments. Preferably, micronized zinc oxide is used. Typical examples are zinc oxides, such as, for example, zinc oxide neutral, zinc oxide NDM (Symrise) or Z-Cote® (BASF) or SUNZnO-AS and SUNZnO-NAS (Sunjun Chemical Co. Ltd.). Further suitable UV photoprotective filters can be found in the review by P. Finkel in SÖFW-Journal 122, 543 (1996) and Parf. Kosm. 3, 11 (1999).

Besides the two aforementioned groups of primary photoprotective substances, it is also possible to use secondary photoprotective agents of the antioxidant type, which interrupt the photochemical reaction chain which is triggered when UV radiation penetrates into the skin. Typical examples thereof are amino acids (e.g. glycine, histidine, tyrosine, tryptophan) and derivatives thereof, imidazoles (e.g. urocanic acid) and derivatives thereof, peptides such as D,L-carnosine, D-carnosine, L-carnosine and derivatives thereof (e.g. anserine), carotenoides, carotenes (e.g. α-carotene, β-carotene, lycopene) and derivatives thereof, chlorogenic acid and derivatives thereof, lipoic acid and derivatives thereof (e.g. dihydrolipoic acid), aurothioglucose, propylthiouracil and other thiols (e.g. thioredoxin, glutathione, cysteine, cystine, cystamine and the glycosyl, N-acetyl, methyl, ethyl, propyl, amyl, butyl and lauryl, palmitoyl, oleyl, γ-linoleyl, cholesteryl and glyceryl esters thereof) and salts thereof, dilauryl thiodipropionate, distearyl thiodipropionate, thiodipropionic acid and derivatives thereof (esters, ethers, peptides, lipids, nucleotides, nucleosides and salts), and sulfoximine compounds (e.g. buthionine sulfoximines, homocysteine sulfoximine, butionine sulfones, penta-, hexa-, heptathionine sulfoximine) in very low tolerated doses (e.g. pmol to mol/kg), also (metal) chelating agents (e.g. α-hydroxy fatty acids, palmitic acid, phytic acid, lactoferrin), α-hydroxy acids (e.g. citric acid, lactic acid, malic acid), humic acid, bile acid, bile extracts, bilirubin, biliverdin, EDTA, EGTA and derivatives thereof, unsaturated fatty acids and derivatives thereof (e.g. gamma-linolenic acid, linoleic acid, oleic acid), folic acid and derivatives thereof, ubiquinone and ubiquinol and derivatives thereof, vitamin C and derivatives (e.g. ascorbyl palmitate, Mg ascorbyl phosphate, ascorbyl acetate), tocopherols and derivatives (e.g. vitamin E acetate), vitamin A and derivatives (vitamin A palmitate), and coniferyl benzoate of benzoin resin, rutinic acid and derivatives thereof, α-glycosylrutin, ferulic acid, furfurylideneglucitol, carnosine, butylhydroxytoluene, butylhydroxyanisole, nordihydroguaiacic acid, nordihydroguaiaretic acid, trihydroxybutyrophenone, uric acid and derivatives thereof, mannose and derivatives thereof, superoxide dismutase, zinc and derivatives thereof (e.g. ZnO, ZnSO4) selenium and derivatives thereof (e.g. selenomethionine), stilbenes and derivatives thereof (e.g. stilbene oxide, trans-stilbene oxide) and the derivatives suitable according to the invention (salts, esters, ethers, sugars, nucleotides, nucleosides, peptides and lipids) of these specified active ingredients.

In one embodiment of the invention, the emulsion concentrates according to the invention comprise at least one biogenic active ingredient as further constituent.

Biogenic active ingredients are to be understood as meaning, for example, tocopherol, tocopherol acetate, tocopherol palmitate, ascorbic acid, (deoxy)ribonucleic acid and fragmentation products thereof, β-glucans, retinol, bisabolol, allantoin, phytantriol, panthenol, AHA acids, amino acids, ceramides, pseudoceramides, essential oils, plant extracts, such as, for example, prune extract, bambara nut extract and vitamin complexes.

In one preferred embodiment of the invention, the dispersions according to the invention comprise at least one compound selected from vitamins, allantoin, bisabolol and plant extracts as biogenic active ingredient.

In one preferred embodiment of the invention, the dispersions according to the invention comprise at least one compound selected from tocopherol, tocopherol acetate, tocopherol palmitate, ascorbic acid, β-glucans, retinol, bisabolol, allantoin, phytantriol, panthenol, AHA acids, plant extracts and mixtures thereof as biogenic active ingredient.

In one embodiment of the invention, the emulsion concentrates according to the invention comprise at least one thickener as further constituent.

Suitable thickeners are, for example, Aerosil grades (hydrophilic silicas), polysaccharides, in particular xanthan gum, guar-guar, agar-agar, alginates and tyloses, carboxymethylcellulose and hydroxyethyl- and hydroxypropylcellulose, polyvinyl alcohol, polyvinylpyrrolidone and bentonites such as, for example, Bentone® Gel VS-5PC (Rheox).

In one embodiment of the invention, the emulsion concentrates according to the invention comprise at least one deodorizing active ingredient as further constituent.

Deodorizing active ingredients counteract, mask or eliminate body odors. Body odors arise as a result of the effect of skin bacteria on apocrine perspiration, whereupon unpleasant smelling degradation products are formed. Accordingly, suitable deodorizing active ingredients are, inter alia, antimicrobial agents, enzyme inhibitors, odor absorbers or odor maskers.

Suitable insect repellents are, for example, N,N-diethyl-m-toluamide, 1,2-pentanediol or ethyl 3-(N-n-butyl-N-acetylamino)propionate, which is sold under the name Insect Repellent® 3535 by Merck KGaA, and also butylacetylaminopropionates.

A suitable self-tanning agent is dihydroxyacetone. Suitable tyrosine inhibitors, which prevent the formation of melanin and are used in depigmentation compositions, are, for example, arbutin, ferulic acid, kojic acid, coumaric acid and ascorbic acid (vitamin C).

Dyes which can be used are the substances approved and suitable for cosmetic purposes. Examples are Cochineal Red A (C.I. 16255), Patent Blue V (C.I. 42051), indigotin (C.I. 73015), chlorophyllin (C.I. 75810), quinoline yellow (C.I. 47005), titanium dioxide (C.I. 77891), indanthrene blue RS (C.I. 69800) and madder lake (C.I. 58000). These dyes are usually used in concentrations of 0.001 to 0.1% by weight, based on the total mixture.

Suitable perfume oils which may be mentioned are mixtures of natural and synthetic fragrances. Natural fragrances are extracts of flowers, stems and leaves, fruits, fruit peels, roots, woods, herbs and grasses, needles and branches, resins and balsams. Also suitable are animal raw materials, such as, for example, civet and castoreum, and also synthetic fragrance compounds of the ester, ether, aldehyde, ketone, alcohol and hydrocarbon types.

Further constituents of the emulsion concentrates (such as e.g. preservatives, cosmetic active ingredients, UV filters etc.) are to be added either via the water phase or via the lipophilic phase depending on their solubility.

Preparation of the Emulsion Concentrates According to the Invention

The preparation of the emulsion concentrates according to the invention preferably takes place in accordance with the process described in EP 0723432 B1. It is therefore preferred to select the water-insoluble oil component (A), the hydrophilic nonionic emulsifier (B) and the lipophilic coemulsifier (C) such that the emulsions prepared therewith have a phase inversion temperature in the range below 100° C. The emulsifiers (B) and coemulsifiers (C) are mixed with the water-insoluble component (A) and heated up to 5° C. above the phase inversion temperature. Then, water and polyol (D) of approximately the same temperature are added with stirring—or vice versa, the mixture of oil component, emulsifier and coemulsifier is stirred into the water with polyol heated to 5° C. above phase inversion temperature. Alternatively, the emulsification can also be carried out below the phase inversion temperature and the emulsion then brought up to 5° C. above the phase inversion temperature. After the cooling, a very finely divided emulsion concentrate is then obtained.

The preparation of the emulsion concentrates can take place in accordance with customary emulsifying techniques known to the person skilled in the art, for example high-pressure homogenization may be mentioned. The preparation preferably takes place according to the so-called phase inversion method (PIT). PIT technology is described in the prior art.

The emulsion concentrates according to the invention usually have a viscosity of greater than or equal to 200 mPas, preferably greater than or equal to 400 mPas (measured using a Brookfield rotary viscometer model RVF, spindle 4, 10 rpm, 20° C.).

Use of the Emulsion Concentrates

The emulsion concentrates according to the invention can be used directly as cosmetic or pharmaceutical preparations. The invention therefore further provides the use of the emulsion concentrates according to the invention as cosmetic or pharmaceutical preparations.

The emulsion concentrates according to the invention are finely divided and very storage-stable; they are consequently very particularly suitable as pre-prepared emulsion building block which, on account of its flowability, is highly suited for storage and transportation to a processing site with little technical equipment, in order there to prepare, using the simplest possible means, useful cosmetic and pharmaceutical emulsions, in particular oil-in-water emulsions.

Accordingly, the invention further provides the use of the emulsion concentrates according to the invention for producing cosmetic or pharmaceutical preparations.

The emulsion concentrate according to the invention is suitable in particular for the preparation of cosmetic or pharmaceutical oil-in-water emulsions. In this connection, it is possible to incorporate either the continuous aqueous phase or the lipophilic phase, or both, into the emulsion concentrate without the further introduction of heat.

The aqueous phase with which the emulsion concentrate is diluted can comprise, in dissolved form, any desired water-soluble constituents, e.g. water-soluble cosmetic active ingredients, water-soluble proteins or protein degradation products, preservatives, dyes, fragrances, magnesium salts or other customary water-soluble components. Preferably, the aqueous, continuous phase comprises a water-soluble, natural or synthetic polymer which improves the cosmetic properties of the emulsions by increasing the viscosity. A particularly effective combination of hydrocolloids for improving the cosmetic properties of such emulsions is a mixture of nonionic cellulose ethers, e.g. hydroxypropylcellulose and crosslinked acrylic acid polymers, as are available, for example, under the trade name Carbopol® (cf. DE 3521713 A1).

The lipophilic phase with which the emulsion concentrate is diluted can comprise any desired lipophilic constituents, e.g. lipophilic cosmetic active ingredients. All compounds suitable as component (A) are suitable as lipophilic phase.

As a rule, 1 to 50% by weight, preferably 2 to 30% by weight, in particular 4 to 10% by weight, of the emulsion concentrate are used for producing the cosmetic or pharmaceutical preparations.

Cosmetic Preparations

The invention further provides cosmetic or pharmaceutical preparations which comprises water-insoluble oil components (A), hydrophilic nonionic emulsifiers (B), lipophilic coemulsifiers (C), polyols (D) in the weight ratio A:B:C:D=1:(0.25-0.6):(0.25-0.6):(0.45-0.65).

Surprisingly, it has been found that through the ratio according to the invention of the components relative to one another, stable, finely divided preparations, in particular oil-in-water emulsions, can be obtained.

The preparations according to the invention can be produced, for example, by appropriately diluting the emulsion concentrates according to the invention. In the simplest case, the dilution takes place with water such that the ratio according to the invention of the components is not changed. However, it is also likewise possible to produce the preparations according to the invention by processes known to the person skilled in the art, such as, for example, simple mixing of components (A) to (D) and optionally water or by known processes of emulsion preparation.

Use for the Coating of Substrates

The emulsion concentrates according to the invention and also the cosmetic or pharmaceutical preparations according to the invention are suitable in particular for the coating of substrates.

The emulsion concentrates and the preparations are particularly suitable for application to papers, wipes, textiles and cotton wool products which are used in the babycare and baby hygiene sector and also in the field of make-up removal, in particular of eye make-up removal, in the area of women's hygiene (tampons, sanitary towels, panty liners) and in the area of body hygiene (toilet paper, moist toilet paper).

The application therefore further provides the use of the emulsion concentrates according to the invention or of the preparations according to the invention on papers, nonwovens and wovens. Included here according to the invention are all types of paper, nonwovens and wovens which are known to the person skilled in the art, and products which can be produced therefrom, such as, for example, toilet paper, paper tissues, tissues, wipes, cotton wool, cotton wool pads, make-up removers, tampons, sanitary towels, panty liners, diapers, babycare wipes, baby cleaning wipes, textiles, etc.

The invention likewise provides paper, nonwoven and woven products for bodycare and body cleaning which comprise water-insoluble oil components (A), hydrophilic nonionic emulsifiers (B), lipophilic coemulsifiers (C), polyols (D) in the weight ratio A:B:C:D=1:(0.25-0.6):(0.25-0.6):(0.45-0.65).

Substrates of these paper, nonwoven and woven products which may be mentioned by way of example are: supports made of textile fiber, e.g. made of natural fiber, such as cellulose, silk, wool, regenerated cellulose (viscose, rayon), cellulose derivatives and/or synthetic fibers, such as, for example, polyester, polypropylene, polyethylene terephthalate, polyamide, polyolefin, polyacrylonitrile fibers or mixtures of such fibers, woven or nonwoven.

The products according to the invention can be produced by processes known to the person skilled in the art. Application of the emulsion concentrates according to the invention or of the preparations according to the invention to the paper, nonwoven and woven products according to the invention for bodycare and body cleaning takes place here by methods known to the person skilled in the art, such as, for example, impregnation, saturation, immersion, spraying, stripping or coating. This can take place either at room temperature or else at elevated temperatures. The emulsion concentrates according to the invention or the preparations according to the invention can be diluted prior to application to the paper, nonwoven and woven substrate and, if desired, the resulting paper, nonwoven and woven product can then be dried.

EXAMPLES

The following examples aim to illustrate the invention in more detail:

Preparation of Emulsion Concentrates:

The hydrophilic emulsifiers (B) and lipophilic coemulsifiers (C) were heated together with the oil component (A) up to 95° C. Then, the water and the polyol (D) at the same temperature were added and intensively mixed. After cooling to 20° C., a finely divided emulsion was obtained. The viscosity was measured in each case 5 hours after preparation of the emulsion using a rotary viscometer.

Table 1 shows the composition of the examples according to the invention and also the results of the stability measurements. Table 2 lists the ratios of the components (A), (B), (C) and (D).

Only the emulsion concentrates according to the invention are stable upon storage.

TABLE 1

Emulsion concentrates (all data in % by weight based on the total weight of the concentrate):

| Component (INCI) | 1 | 2 | 3 | 4 | 5 | 6 | C1 |
|---|---|---|---|---|---|---|---|
| (B) Ceteareth-12 | 1.0 | 3.0 | 2.0 | 1.5 | 1.5 | 1.0 | 1.0 |
| (B) Ceteareth-20 | 9.0 | 6.0 | 10.0 | 8.0 | 8.0 | 8.0 | 6.5 |
| (C) Cetearyl alcohol | 7.0 | 4.0 | 5.5 | 4.0 | 5.0 | 4.5 | 7.0 |
| (C) Glyceryl stearate | 2.0 | 5.0 | 5.5 | 6.0 | 5.0 | 4.5 | 7.0 |

TABLE 1-continued

Emulsion concentrates (all data in % by weight based on the total weight of the concentrate):

| Component (INCI) | 1 | 2 | 3 | 4 | 5 | 6 | C1 |
|---|---|---|---|---|---|---|---|
| (A) Cetearyl Isononanoate | 18.0 | | | 14.0 | | 25.0 | 18.0 |
| (A) Coco caprylate/Caprate | | 15.0 | 11.0 | | 12.0 | | |
| (A) Paraffinium Perliquidum | | | | | 5.0 | | |
| (A) Caprylic/capric triglyceride | | | | | | 6.0 | |
| (A) Isopropyl palmitate | | | 11.0 | | | | |
| (D) Glycerin | 10.0 | 12.0 | 10.5 | 10.0 | 11.0 | 11.5 | 5.0 |
| Water | 53.0 | 50.0 | 44.5 | 51.5 | 51.5 | 45.5 | 55.5 |
| pH adjuster; preservative | pH 3.0-3.3; q.s. | | | | | | |
| Stability data | Stable for 3 months at 40° C. | | | | | | Separation <1 week |
| Viscosity (RT) (Brookfield RVF, spindle 4, 10 rpm), [mPa * s] | 600 | 800 | 900 | 1800 | 2000 | 2500 | — |
| Viscosity (40° C.) (Brookfield RVF, spindle 4, 10 rpm), [mPa * s] | 2500 | 1800 | 1700 | 2100 | 2300 | 2800 | — |
| Particle size (Coulter LS) [nm] | 105 | 110 | 95 | 115 | 110 | 120 | 500 |

TABLE 2

| | (A):(B):(C):(D) ratio |
|---|---|
| Example 1 | 1:0.56:0.50:0.56 |
| Example 2 | 1:0.45:0.45:0.6 |
| Example 3 | 1:0.54:0.50:0.48 |
| Example 4 | 1:0.50:0.53:0.53 |
| Example 5 | 1:0.53:0.55:0.61 |
| Example 6 | 1:0.36:0.36:0.46 |
| Comparative example C1 | 1:0.42:0.77:0.28 |

The invention claimed is:

1. An emulsion concentrate consisting essentially of, based on the total weight of the concentrate:
   (A) less than 50% by weight in total of a water-insoluble oil component,
   (B) 1 to 25% by weight of a hydrophilic nonionic emulsifier;
   (C) 1 to 25% by weight of a lipophilic coemulsifer;
   (D) 8 to 15% of a polyol,
   (E) 35 to 55% by weight of an aqueous phase, and
   (F) optionally, up to 25% by weight of an additional ingredient, wherein the additional ingredient selected from the group consisting of a preservative, a biogenic active ingredient, a UV photoprotective filter, a thickener, a superfatting agent, a stabilizer, a polymer, an antioxidant, a deodorant, a film former, a swelling agent, an insect repellant, a hydrotrope, a solubilizer, a perfume oil, a dye, and combinations thereof,
   wherein the total of (A), (B), (C) and (D) are present in a weight ratio A:B:C:D=1:(0.25-0.6):(0.25-0.6):(0.45-0.65), wherein if an additional ingredient (F) also falls under (A), (B), (C) or (D), then the additional ingredient (F) is counted toward (A), (B), (C) or (D),
   wherein the emulsion concentrate is flowable and pumpable at 20° C., and
   wherein the water-insoluble component (A) is selected from the group consisting of hydrocarbons which are liquid at 30° C., dialkyl ethers, C6-C22 fatty acids esterified with C6-C22 fatty alcohols, dialkyl carbonates, Guerbet alcohols, silicone oils, esters of linear C6-22 fatty acids with branched alcohols, triglycerides based on C6-10 fatty acids and mixtures thereof, with the proviso that the total of (A), (B), (C), (D), (E), and (F) is 100%.

2. The emulsion concentrate of claim 1 wherein at least 60% by weight of the water-insoluble oil component (A) has an average polarity of greater than or equal to 20 mN/m and less than or equal to 30 mN/m.

3. The emulsion concentrate of claim 1, wherein said hydrophilic nonionic emulsifier (B) is selected from the group consisting of ethoxylated linear fatty alcohols, ethoxylated fatty acids, ethoxylated fatty acid partial glycerides, ethoxylated sorbitan fatty acid esters and ethoxylated alkyl (oligo)glycosides, and wherein the compounds have an HLB value of 11-20.

4. The emulsion concentrate of claim 1, wherein said lipophilic coemulsifier (C) is selected from the group consisting of saturated fatty alcohols having 12-24 carbon atoms, partial esters of polyols having 3-6 carbon atoms, fatty acids having 12-24 carbon atoms and mixtures thereof.

5. The emulsion concentrate of claim 1, wherein said polyol comprises polyhydric alcohols which contain 2 to 18 carbon atoms.

6. The emulsion concentrate of claim 5, wherein said polyol comprises 2 to 6 hydroxyl groups.

7. The emulsion concentrate of claim 5, wherein said polyol comprises at least one compound selected from the group consisting of glycerol, 1,2-propylene glycol, sorbitol, butylene glycol and hexylene glycol.

8. The emulsion concentrate of claim 1, wherein:
   (A) the water-insoluble oil component is present in an amount in the range of 5 to 25 weight %, comprising one or more of: cetearyl isononanoate, cococaprylate/caprate, mineral oil, caprylic/capric triglyceride, and isopropyl palmitate, (B) the hydrophilic nonionic emulsifier is present in an amount in the range of 5 to 20 weight %, comprising one or more addition products of 8-30 mol of ethylene oxide onto linear fatty alcohols having 12-22 carbon atoms;
(C) the lipophilic coemulsifer is present in an amount in the range of 8 to 15 weight %, comprising one or more partial glycerides of C12 to C22 fatty acids with glycerol, and saturated fatty alcohols having 16-22 carbon atoms; and
(D) the polyol is present in an amount in the range of 8 to 15 weight %, has 2 to 6 hydroxyl groups per molecule and consists of 2 to 6 carbon atoms.

9. A cosmetic or pharmaceutical preparation comprising:
a cosmetic or pharmaceutical ingredient; and
an emulsion concentrate consisting essentially of, based on the total weight of the concentrate
(A) less than 50% by weight in total of a water-insoluble oil component;
(B) 1 to 25% by weight of a hydrophilic nonionic emulsifier;
(C) 1 to 25% by weight of a lipophilic coemulsifier;
(D) 8 to 15% by weight of a polyol;
(E) 35 to 55% by weight of an aqueous phase, and
(F) optionally, up to 25% by weight of an additional ingredient, wherein the additional ingredient selected from the group consisting of a preservative, a biogenic active ingredient, a UV photoprotective filter, a thickener, a superfatting agent, a stabilizer, a polymer, an antioxidant, a deodorant, a film former, a swelling agent, an insect repellant, a hydrotrope, a solubilizer, a perfume oil, a dye, and combinations thereof,
wherein the weight ratio A:B:C:D=1:(0.25-0.6):(0.25-0.6):(0.45-0.65), wherein if an additional ingredient (F) also falls under (A), (B), (C) or (D), then the additional ingredient (F) is counted toward (A), (B), (C) or (D),
wherein the emulsion concentrate is flowable and pumpable at 20° C., and
wherein the water-insoluble component (A) is selected from the group consisting of hydrocarbons which are liquid at 30° C., dialkyl ethers, C6-C22 fatty acids esterified with C6-C22 fatty alcohols, dialkyl carbonates, Guerbet alcohols, silicone oils, esters of linear C6-22 fatty acids with branched alcohols, triglycerides based on C6-10 fatty acids, and mixtures thereof, with the proviso that the total of (A), (B), (C), (D), (E), and (F) is 100%.

10. The cosmetic or pharmaceutical preparation of claim 9, wherein:
(A) the water-insoluble oil component is present in an amount in the range of 5 to 25 weight %, comprising one or more of: cetearyl isononanoate, cococaprylate/caprate, mineral oil, caprylic/capric triglyceride, and isopropyl palmitate,
(B) the hydrophilic nonionic emulsifier is present in an amount in the range of 5 to 20 weight %, comprising one or more addition products of 8-30 mol of ethylene oxide onto linear fatty alcohols having 12-22 carbon atoms;
(C) the lipophilic coemulsifer is present in an amount in the range of 8 to 15 weight %, comprising one or more partial glycerides of C12 to C22 fatty acids with glycerol, and saturated fatty alcohols having 16-22 carbon atoms; and
(D) the polyol is present in an amount in the range of 8 to 15 weight %, has 2 to 6 hydroxyl groups per molecule and consists of 2 to 6 carbon atoms.

11. A paper, nonwoven or woven product for bodycare and cleansing comprising:
a substrate; and
an emulsion concentrate consisting essentially of, based on the total weight of the concentrate
(A) less than 50% by weight in total of a water-insoluble oil component;
(B) 1 to 25% by weight of a hydrophilic nonionic emulsifier;
(C) 1 to 25% by weight of a lipophilic coemulsifier;
(D) 8 to 15% by weight of a polyol;
(E) 35 to 55% by weight of an aqueous phase, and
(F) optionally, up to 25% by weight an additional ingredient selected from the group consisting of a preservative, a biogenic active ingredient, a UV photoprotective filter, a thickener, a superfatting agent, a stabilizer, a polymer, an antioxidant, a deodorant, a film former, a swelling agent, an insect repellant, a hydrotrope, a solubilizer, a perfume oil, a dye, and combinations thereof,
wherein the weight ratio A:B:C:D=1:(0.25-0.6):(0.25-0.6):(0.45-0.65), wherein if an additional ingredient (F) also falls under (A), (B), (C) or (D), then the additional ingredient (F) is counted toward (A), (B), (C) or (D), and wherein the water-insoluble component (A) is selected from the group consisting of hydrocarbons which are liquid at 30° C., dialkyl ethers, C6-C22 fatty acids esterified with C6-C22 fatty alcohols, dialkyl carbonates, Guerbet alcohols, silicone oils, esters of linear C6-22 fatty acids with branched alcohols, triglycerides based on C6-10 fatty acids and mixtures thereof, with the proviso that the total of (A), (B), (C), (D), (E), and (F) is 100%.

12. The paper, nonwoven or woven product for bodycare and cleansing of claim 11, wherein:
(A) the water-insoluble oil component is present in an amount in the range of 5 to 25 weight %, comprising one or more of: cetearyl isononanoate, cococaprylate/caprate, mineral oil, caprylic/capric triglyceride, and isopropyl palmitate,
(B) the hydrophilic nonionic emulsifier is present in an amount in the range of 5 to 20 weight %, comprising one or more addition products of 8-30 mol of ethylene oxide onto linear fatty alcohols having 12-22 carbon atoms;
(C) the lipophilic coemulsifer is present in an amount in the range of 8 to 15 weight %, comprising one or more partial glycerides of C12 to C22 fatty acids with glycerol, and saturated fatty alcohols having 16-22 carbon atoms; and
(D) the polyol is present in an amount in the range of 8 to 15 weight %, has 2 to 6 hydroxyl groups per molecule and consists of 2 to 6 carbon atoms.

13. A method of preparing a cosmetic and/or pharmaceutical preparation comprising incorporating the emulsion concentrate of claim 1 in a cosmetic and/or pharmaceutical preparation.

14. A method of preparing a cosmetic and/or pharmaceutical preparation comprising incorporating the emulsion concentrate of claim 1 in a cosmetic and/or pharmaceutical preparation, wherein the resulting preparation is an oil-in-water emulsion.

15. A method for coating a substrate comprising coating a substrate with the emulsion concentrate of claim 1.

16. A method for coating a substrate comprising coating a substrate with the cosmetic and/or pharmaceutical preparation of claim 9.

* * * * *